United States Patent [19]
Berndt

[11] Patent Number: 5,371,016
[45] Date of Patent: Dec. 6, 1994

[54] DETECTING BIOLOGICAL ACTIVITIES IN CULTURE VIALS

[75] Inventor: Klaus W. Berndt, Stewartstown, Pa.

[73] Assignee: Becton Dickinson and Company, Franklin Lakes, N.J.

[21] Appl. No.: 53,938

[22] Filed: Apr. 26, 1993

[51] Int. Cl.⁵ .................. C12M 1/34; G01J 3/433
[52] U.S. Cl. ................... 435/291; 435/296; 435/808; 356/318; 250/461.2
[58] Field of Search ............ 435/34, 291, 296, 808; 356/317, 318, 417; 250/461.2

[56] References Cited

U.S. PATENT DOCUMENTS

| | | | |
|---|---|---|---|
| 4,284,355 | 8/1981 | Hansen et al. | 250/461.2 |
| 4,849,172 | 7/1989 | Yafuso et al. | 422/58 |
| 4,968,148 | 11/1990 | Chow et al. | 356/427 |
| 5,143,853 | 9/1992 | Walt | 435/808 |
| 5,155,019 | 10/1992 | Sussman et al. | 435/808 |
| 5,164,796 | 11/1992 | DiGuiseppi et al. | 435/34 |
| 5,217,875 | 6/1993 | Karpf et al. | 435/291 |
| 5,217,876 | 6/1993 | Turner et al. | 435/808 |

Primary Examiner—Donald E. Czaja
Assistant Examiner—Milton I. Cano
Attorney, Agent, or Firm—Alan W. Fiedler

[57] ABSTRACT

An apparatus for detecting microorganisms in a plurality of sealable containers adapted to sustain microorganism growth includes a single light source such as a laser with a two-dimensional laser deflector directing an output beam component from the laser serially towards each of the containers. A sensor is spread along an inner surface of the containers. The selective emission of a sensor is monitored to determine whether biological activity is present in a container. A disclosed embodiment includes the use of a high-frequency modulator and decay time sensors. Biological activity is determined by monitoring the decay time of the sensors.

13 Claims, 5 Drawing Sheets

DETECTING BIOLOGICAL ACTIVITIES IN CULTURE VIALS

BACKGROUND OF THE INVENTION

The present invention relates to a non-invasive method and to an apparatus for detecting biological activities in a bodily fluid specimen sample, such as blood or sputum. Specimen samples and a culture medium are introduced into sealable containers, such as vials, and are then exposed to conditions enabling a variety of metabolic, physical, and chemical changes to take place in time presence of microorganisms within the sample.

The presence of a biologically active agent, such as bacteria in a patient's body fluids, especially blood, is generally determined using culture vials. A small quantity of the bodily fluid is injected through an enclosing rubber septum into a sterile vial containing a culture medium. The vial is incubated at 37° C. and monitored for microorganism growth.

A technique used to detect the presence of microorganisms involves visual inspection. Generally, visual inspection involves monitoring the turbidity or eventual color changes of tile liquid suspension of a bodily fluid and culture medium. Known sensors respond to changes in pH, oxygen concentration, or carbon dioxide concentration by changing their reflectivity, opacity, color or by changing their fluorescence intensity. The outputs from these sensors are generally based upon light intensity measurements. Light sources used to excite the sensors or the photodetectors used to monitor intensities exhibit aging effects over time. This means that errors may occur. Additionally, vial positioning is extremely important when intensity measurements are required. Even minor vial mis-positioning may affect detection measurements. Further, it is not always possible to make incubators completely light tight. Random light entering an incubator may cause dark currents, also affecting detection measurements.

Disadvantages of intensity-based methods may be overcome by using modulated excitation light in combination with sensors that change their fluorescence decay time in response to changing pH, oxygen concentration, carbon dioxide concentration, or in response to other biological activities. Using this approach, intensity measurements are replaced with time measurements, so intensity changes do not influence the results. However, fluorescence decay time sensors require high-brightness short-wavelength light sources (550 nm or shorter) that are intensity-modulated at very high frequencies (typically above 100 MHz). Because such a light source/modulator combination is expensive, vials would have to be moved to the light source instead of having a light source for each vial. Moving parts, and the relatively long time interval between successive measurements for each vial are additional concerns. Nor is it likely that inexpensive high-brightness short-wavelength semiconductor diode lasers will be developed soon.

In known automated non-invasive culture systems, individual light sources, spectral excitation/emission filters, and photodetectors are arranged by each vial. This results in station sensitivity variations from one vial to the next. Therefore, extensive and time-consuming calibration procedures are required to operate such systems. In addition, flexible electrical cables are required to connect the individual sources and detectors with the rest of the instrument. With the large number of light sources, typically 240 or more per instrument, maintenance can become very cumbersome and expensive when individual light sources start to fail.

The method and apparatus of the present invention solves the inherent problems of the prior art, using a single high energy light source in conjunction with a light beam deflector, to detect biological activity in a large number of vials. Manufacturability and the ability to detect biological activity are increased while cost is lowered.

SUMMARY OF THE INVENTION

The present invention relates to automated systems for the detection of biological activities in fluid specimen samples of blood, sputum, or other body fluids.

An apparatus constructed according to the present invention includes a plurality of sealable containers or vials adapted to sustain microorganism growth. Specimen samples placed in the vials are then arranged on a tipping rack. The tipping rack agitates the vials to promote microorganism growth. A plurality of such racks are used because a single tipping rack would have considerable unwanted mass.

In the disclosed embodiments, a sensor adapted to respond to biological activity is spread along an interior surface of each vial to react with the sample. A high energy light source generates an output beam which is directed by a two-dimensional deflector toward a preselected sensor associated with a vial. The sensor generates a selective emission in the presence of microorganism growth. A preferred sensor selectively generates a fluorescence emission, but other possible selective emission sensors include those that change their reflectivity, opacity, or color in response to biological activity, or the sample itself may be illuminated. In the latter case, no sensor material has to be spread onto the interior vial surface.

Such an apparatus does not have individual light sources, excitation filters, emission filters, or photodetectors at each vial. This increases manufacturability while lowering cost. Preferably, utilizing presently available detection technology, the light source is a green helium neon laser having approximately 1.5 mW of output power and an approximate beam diameter no greater than about 2 mm. The short-wavelength and output power react s favorably with fluorescence sensors. A preferred two-dimensional deflector is a galvanometric laser deflector having high angular resolution and good reproducibility.

A first embodiment of the present invention involves the use of intensity sensors. A presently preferred sensor is a fluorescence sensor. A high energy light source, such as a laser, generates an output beam which is split by a beam splitter into a reference beam component and an output beam component. A laser deflector directs the output beam component off a mirror to a preselected sensor associated with one of the vials. The mirror is used to reduce the size of an incubator containing the vials. In the presence of biological activity the sensor will generate an emission. At least one detector module monitors this emission. A disclosed detector module includes a spectral filter to block short-wavelength or excitation light, a Fresnel lens to collect the sensor emission, and a photodetector. A photocurrent generated by the photodetector is routed to a detector DC meter. A reference photodetector monitors the reference beam component and generates a reference photocurrent which is routed to a reference DC meter. The outputs from the two meters are fed into a control device such as a computer so that a determination regarding microorganism growth may be made. Further, the control device controls the positioning of the laser scanner so that output beam portion is directed serially from sensor to sensor.

In a second embodiment of the present invention intensity detection is replaced with time-resolved detection. A high-frequency intensity modulator is disposed in front of the laser. The modulator is controlled by the computer in conjunction with an amplifier. The output beam passes from the laser through the modulator. The output beam is then split by the beam splitter into an output beam component and a reference beam component. The output beam component is directed using a laser scanner and a mirror. A decay time sensor is associated with each vial. A preferred sensor of this type is a fluorescence decay time sensor. An advantage of such a sensor is that intensity changes resulting from component aging, slight vial mis-positioning, and non light tight incubators do not influence the results. The modulated output beam component reacts with a sensor to generate a modulated emission. The detector module monitors the emission and generates a photocurrent. Similarly, the reference photodetector monitors the modulated reference beam component and generates a reference photocurrent. The two photocurrents are routed to a vector voltmeter which determines the phase shift between the inputs. The output from the vector voltmeter is used by the controller to determine whether biological activity is present. As in the first embodiment, the controller also adjusts the laser deflector.

In a third embodiment, no mirror is used. Instead the laser deflector selectively and directly focuses the output beam component onto each sensor. Further, smaller vials are illustrated. The present invention works equally well with a large number of vials in a very limited space.

BRIEF DESCRIPTION OF THE DRAWINGS

The various features and inventive aspects of the present invention will become more apparent upon reading the following detailed description and claims together with the drawings, wherein reference numerals identify corresponding components, and:

DETAILED DESCRIPTION OF THE PREFERRED EMBODIMENTS

Figure 1:
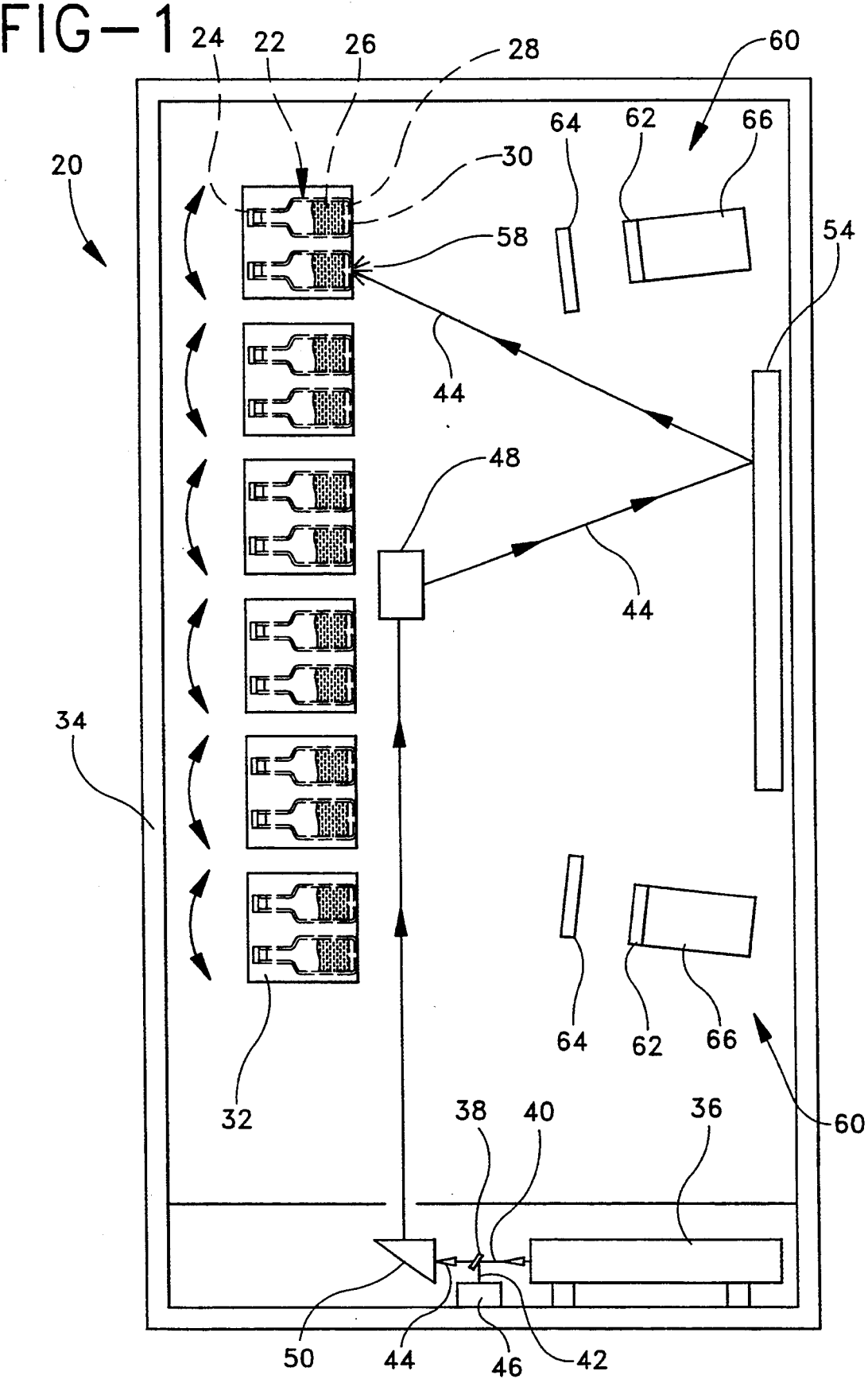
FIG. 1 shows an apparatus for the intensity-based detection of microorganism according to the present invention.

A first preferred embodiment of an apparatus for intensity-based detection of microorganisms is shown in FIG. 1. Apparatus 20 comprises a plurality of containers, such as glass vials 22, each sealed with a septum 24 and containing a medium/bodily fluid mixture 26. A vial 22 contains an intensity-based chemical sensor 28 spread on an inner bottom surface 30. While a fluorescence intensity sensor is illustrated, other sensors which generate a selective emission or change their reflectivity, opacity, or color in the presence of biological activity may also be used. In some cases, the sample itself may be scanned without the use of a separate sensor associated with the vial.

Vials 22 are arranged on a tipping rack 32, with two rows of vials for each rack 32. Tipping racks 32 agitate to promote the growth of microorganisms within vials 22. Tipping racks 32 may be placed in a hold position, such as that shown in FIG. 1, so that a determination of biological activity may be made. Preferably, tipping racks 32 assume the same hold position each time microorganism detection is undertaken. A plurality of tipping racks 32 are used primarily because a tipping rack for as many as 240 vials would have considerable unwanted mass. Contrary to the prior art, apparatus 20 does not require individual light sources, excitation filters, emission filters, and photodetectors for each vial. Therefore, racks 32 contain only vials 22 and no electronic components and, consequently, no electrical wires. This increases manufacturability while lowering cost. Vials 22 and tipping racks 32 are arranged inside an incubator 34 that is used to promote microorganism growth.

Tipping racks 32 have no electronic components because output generated from a single high energy light source, such as a laser 36, reacts with sensors 28 of a large number of vials 22. A beam splitter 38 splits an output beam 40 from laser 36 into components 42 and 44. Reference beam component 42 is directed toward a reference photodetector 46. Photodetector 46 measures the intensity of reference beam component 42 and generates a reference photocurrent value corresponding to the measured intensity. Output beam component 44 is directed toward a two-dimensional light beam deflector 48 by means of a prism 50. In the illustrated embodiment, a 90 degree prism is used. Deflector 48 is adjusted to direct output beam component 44 toward a mirror 54. Output beam component 44 reflects off mirror 54, as determined by deflector 48, to contact and excite a sensor 28 of a selected vial 22. When excited by output beam component 44, a sensor 28 will selectively generate an emission indicating the presence of biological activity. In the illustrated embodiment, a fluorescence emission will be generated by the sensor, increasing in proportion to increased biological activity. Fluorescence intensity chemical sensors 28 are known which react to pH, oxygen concentration, carbon dioxide concentration, or in response to other biological activities.

Mirror 54 reduces the depth of incubator 34 by at least the distance between deflector 48 and mirror 54. This allows a more compact and energy efficient incubator to be used.

Emission 58 from a particular sensor 28 is monitored by at least one detector module 60. A limited number of such modules are needed for many vials 22. In the illustrated embodiment, only two such modules 60 are depicted. Preferably, detector modules 60 are arranged within incubator 34. A detector module 60 includes a collection lens 64, a spectral emission filter 62, and a high-sensitivity photodetector 66. Filter 62 is used block unwanted short-wavelength or excitation radiation that can affect readings. Photodetector 66 measures the intensity of emission 58 and generates a sensor photocurrent value representative of the measured intensity.

The use of laser 36, deflector 48, and a limited number of detector modules 60 to determine the presence of microorganism growth within each of a large number of vials 22 is particularly advantageous. In particular, no mechanical parts have to be moved around. Therefore, excellent long-term instrument reliability is possible. Further, greater accuracy results from using a single calibrated arrangement for many vials in place of intensity measurement devices for each vial. More expensive and precise instrumentation can also be used at an economical cost. In fact, the need for instrument calibration is greatly reduced, if not eliminated by the present invention.

Typically, vials 22 are continuously scanned one by one until either there is a presence of biological activity, or a predetermined period of time, typically five days, have passed. The presence of biological activity in particular vials is indicated by a pronounced change in the measured sensor emission 58. The purpose of the reference photodetector 46 is to compensate for wanted changes in laser intensity.

In one preferred embodiment, laser 36 is a green helium neon (HeNe) laser having a wavelength in the range of about 543.5 nm, with approximately 1.5 mW of output power. The diameter of output beam 40 should be no greater than about 2 mm. The short-wavelength light and output power reacts favorably with a fluorescence sensor 28 in the presence of biological activity. Because of the favorable fluorescence intensity resulting from microorganism growth within a vial 22, a remote high-sensitivity photodetector 66, such as a photomultiplier, may be used to monitor the sensor emission 58 from a large number of vials 22. Even a remote photodetector 66 generates a photocurrent with a sufficiently high signal-to-noise ratio, so that one or two multipliers are sufficient to monitor a large number of culture vials.

If tipping racks 32 containing a total of 240 vials (12 rows and 20 columns) are used, deflector 48 must be able to address a maximum of 20 vials in one direction. Standard two-dimensional galvanometric laser deflectors with extremely high angular resolution and good reproducibility are readily available. Such deflectors are suitable to position output beam component 44 over desired range of approximately 45 degrees to reach any of vials 22 and still have good reproducibility.

To collect as much of sensor emission 58 as possible, large-size Fresnel lenses are used as collection lenses 62. Such lenses are commercially available in different sizes, and at low cost.

Figure 2:
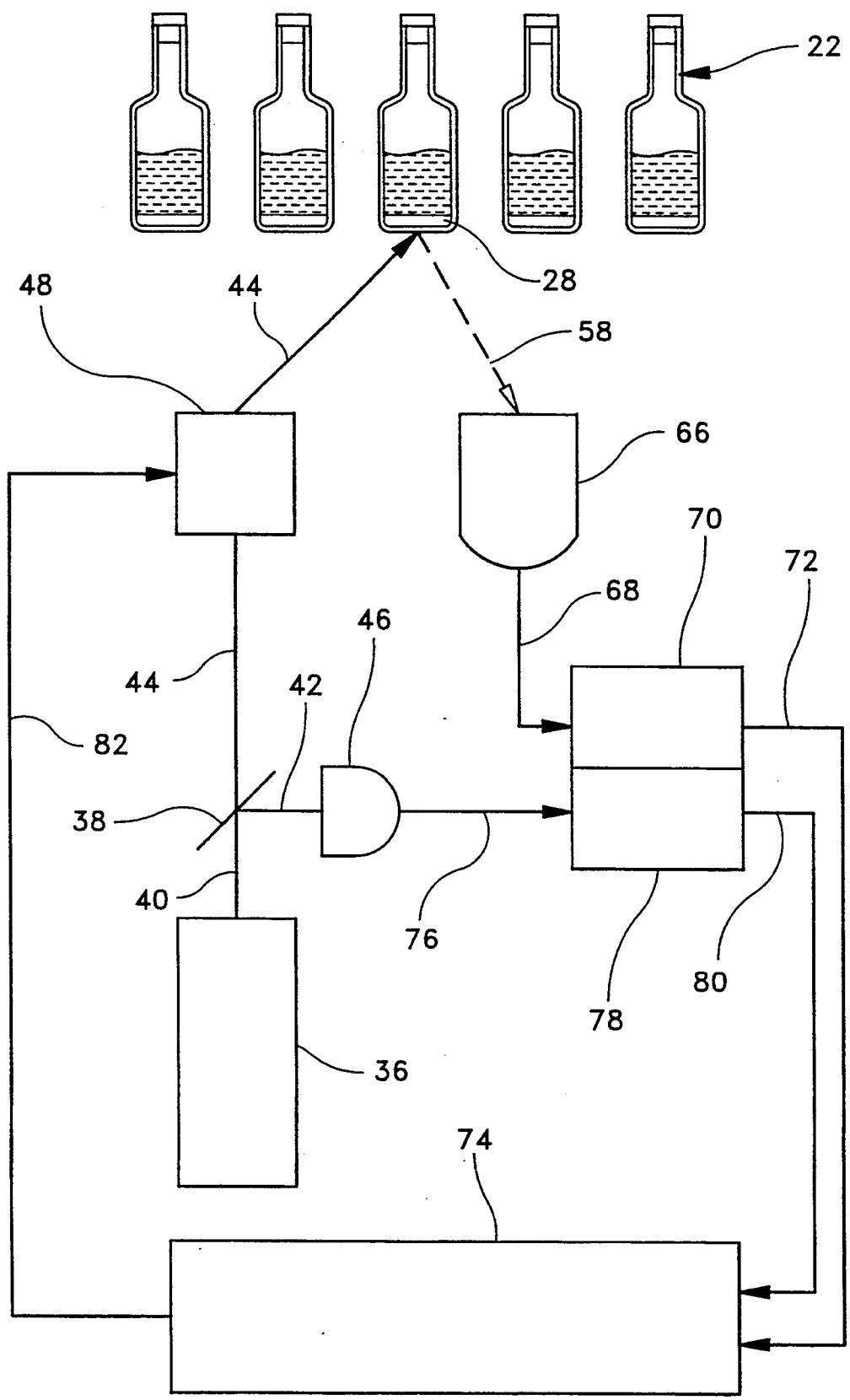
FIG. 2 is a schematic illustrating the main optical and electronic components according to the embodiment of FIG. 1.

As shown schematically in FIG. 2, laser 36 generates an output beam 40. Beam splitter 38 splits output beam 40 into reference beam component 42 and output beam component 44. Deflector 48 directs output beam component 44 to a preselected sensor 28 associated with a vial 22. Sensor 28 then generates an emission 58. Photodetector 66 monitors emission 58 and generates a sensor photocurrent 68. In the illustrated embodiment, this is a fluorescence photocurrent. Photocurrent 68 is routed to a detector DC meter 70. In turn, an output 72 from meter 70 is fed to a control device, such as a computer 74. Reference beam component 42 is directed to reference photodetector 46, which monitors reference beam component 42 and generates a reference photocurrent 76. Photocurrent 76 is routed to a reference DC meter 78. An output 80 from meter 78 is also fed into computer 74. As shown by line 82, besides storing outputs 72 and 80, computer 74 controls the positioning of laser deflector 48 so that deflector 48 selectively directs output beam portion 44 serially from sensor to sensor. Thus, a determination of microorganism growth can be made for each vial.

Figure 3:
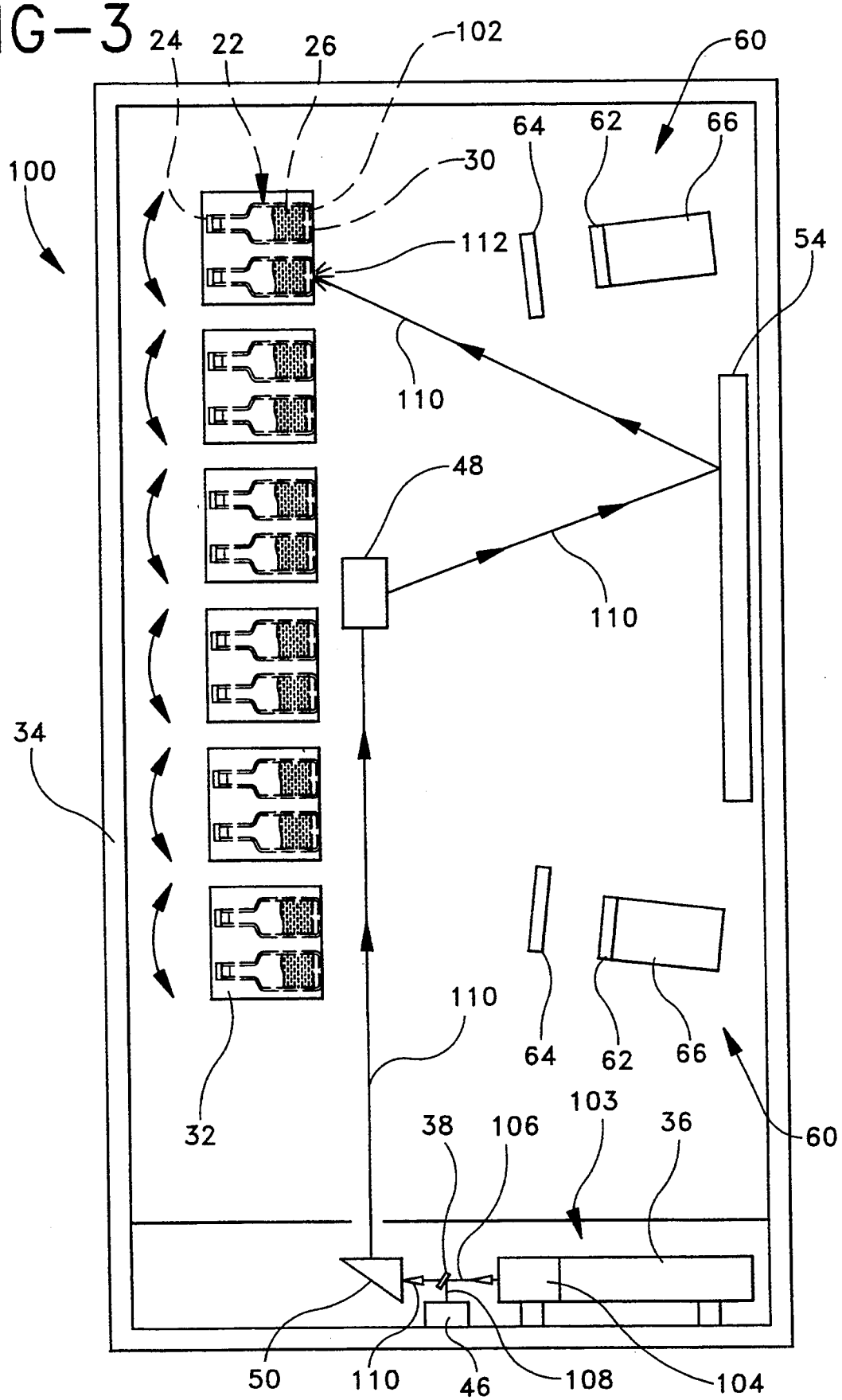
FIG. 3 shows an apparatus for the decay time-based detection of microorganism according to the present invention.

An embodiment of an apparatus 100 for the decay time detection of microorganisms is shown in FIG. 3. Apparatus 100 is similar to apparatus 20 illustrated in FIG. 1. However, a different type of optical sensor, a decay time sensor 102, is disposed on inner bottom surface 30 of each of vials 22. A preferred sensor is a fluorescence decay time sensor, although other sensors may be used. Fluorescence decay time sensors are known which change their decay time in response to changing pH, oxygen concentration, carbon dioxide concentration, or in response to other biological activities. Using this method, intensity measurements are replaced with time measurements, so intensity changes do not influence the results. For sensors 102 to work properly, a modulated light source 103 is comprised of a high-frequency intensity modulator 104 arranged between laser 36 and beam splitter 38. The laser may be the same as that disclosed in the embodiment of FIG. 1. Modulator 104 may be acousto-optic, electro-optic or elasto-optic.

Output 106 from modulated light source 103 is split into components 108 and 110. Reference beam component 108 is directed toward a reference photodetector 46 while output beam component 110 is directed toward a two-dimensional laser deflector 48 by means of a prism 50. Deflector 48 is adjusted to direct output beam component 110 toward a mirror 54. Component 110 reflects off mirror 54 as determined by deflector 48 to contact sensor 102 of a selected vial 22.

A modulated emission 112 selectively generated by a particular sensor 102 is time modulated in response to increasing biological activity. It is the modulation rather than intensity that is primarily monitored by at least one detector module 60. As long as the modulation can be measured, a determination of biological activity can be made. Therefore, minor vial mis-positioning, light source or detector module aging, and dark current changes such as those resulting from outside light leakage into incubator 34, become much less critical when compared to intensity sensors.

Currently available fluorescence decay time sensors require high light modulation frequencies, typically above 100 MHz. In known systems with individual light sources at each vial 22, green light emitting diodes ("LED"s) are used. LEDs cannot be modulated at such high frequencies. In apparatus 100, however, with laser 36, high-frequency intensity modulation may be easily accomplished.

Figure 4:
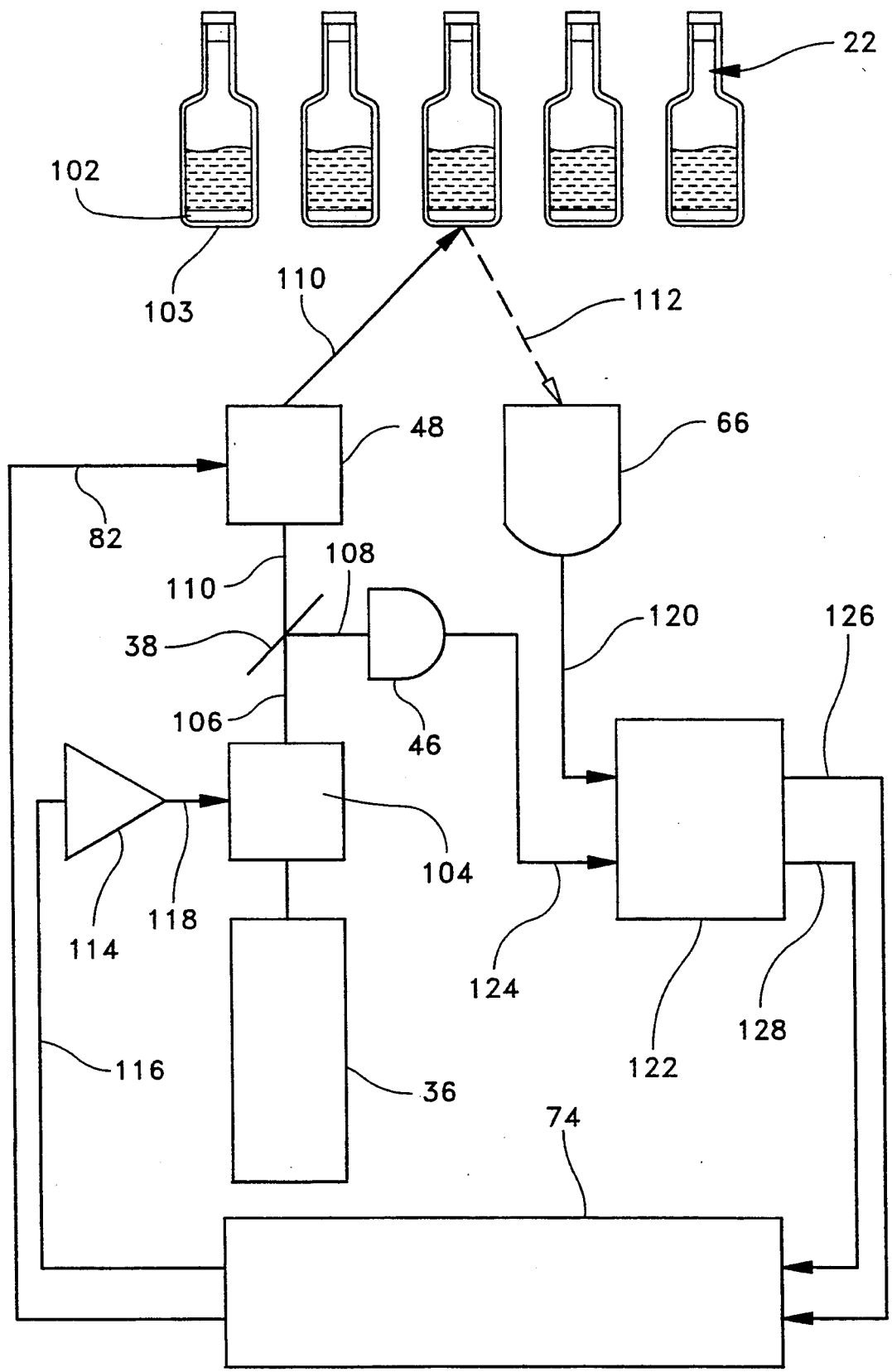
FIG. 4 is a schematic illustrating the main optical and electronic components according to the embodiment of present invention.

As shown schematically in FIG. 4, computer 74 controls modulator 104 using an amplifier 114. Computer 74 sends a signal 116 to amplifier 114, and an output signal 118 from amplifier 114 is sent to modulator 104. Beam splitter 38 splits output beam 106 from modulator 104 into reference beam component 108 and output beam component 110. Output beam component 110 is directed by deflector 48 to a preselected sensor 102 of a vial 22. Sensor 102 selectively generates modulated sensor emission 112. Photodetector 66 monitors sensor emission 112 and generates a modulated photocurrent 120 which is routed to a vector voltmeter 122. Reference photodetector 46 monitors reference beam component 108 and generates a modulated reference photocurrent 124 which is also routed to vector voltmeter 122. Vector voltmeter 122 compares photocurrents 120 and 124 to determine a sensor phase shift and, optionally, sensor intensity. This information is fed into computer 74 via voltmeter outputs 126 and 128 so that a determination may be reached regarding microorganism growth for each vial. As in the embodiment of FIG. 2, computer 74 controls the positioning of deflector 48 via line 82 so that output beam component 110 may be directed from vial to vial.

In FIG. 3, alternatively, a single modulated light source 103 and detector module 60 may be used with many vials having the appropriate sensor 102, although in the illustrated embodiment, two detector modules 60 are shown.

The presence of microorganisms in particular vials is indicated by a pronounced change in the phase shift of the measured sensor emission 112 relative to the reference signal phase 108.

Figure 5:
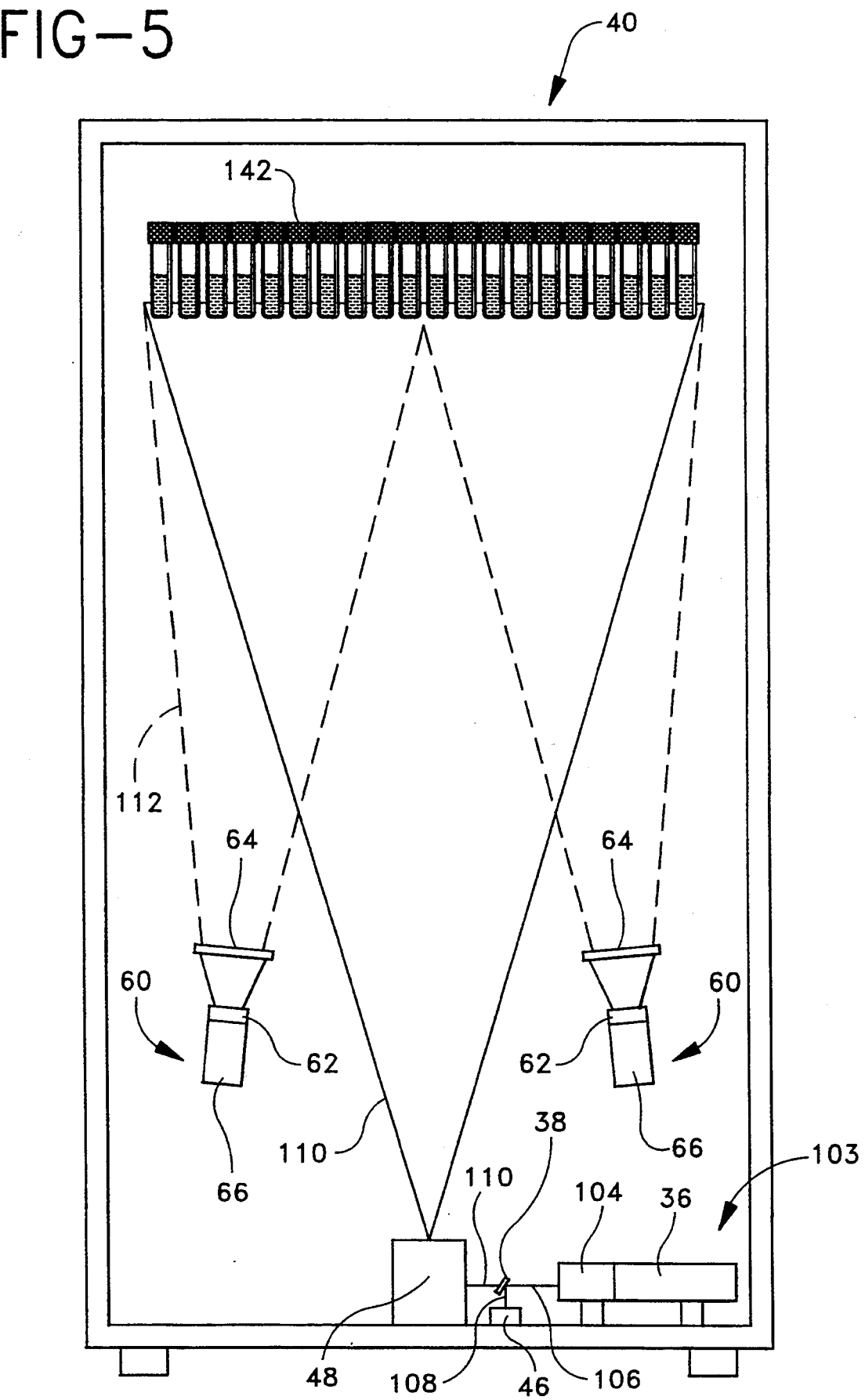
FIG. 5 illustrates a second embodiment for the decay time-based detection of microorganism according to the FIG. 3.

A second embodiment of a decay time microorganism detection apparatus is shown in FIG. 5. A modulated light source 103 comprises a laser 36 and s modulator 104. A beam splitter 38 splits output beam 106 to direct an output beam component 108 to a reference photodetector A6 and an output beam component 110 to a two-dimensional laser deflector 48. No prism 50 or mirror 54, as illustrated in FIGS. 1 and 3, are required. Instead, laser deflector 48 selectively and directly focuses output beam component 110 onto sensor 102 of each vial 142. A laser deflector-based apparatus according to the present invention is particularly advantageous for tuberculosis ("TB") vials because of their reduced size as compared to typical blood culture vials. If a diameter of about 20 mm is assumed for a TB vial, then 625 such vials can be accommodated and monitored within a quadratic array of only 50 by 50 cm.

Preferred embodiments of the present invention have been described. It is to be understood, of course, that variations and modifications may be employed without departing from the scope of the present invention. As discussed, for example, it is possible to use the specimen sample directly for the detection of biological activity. Alternatively, it may be desirable to use a specific sensor which reacts with the specimen sample. Accordingly, the following claims should be studied to learn the true scope of the present invention.

I claim:

1. An apparatus for detecting microorganisms in fluid specimen samples, said apparatus comprising:
   a plurality of sealable containers adapted to sustain microorganism growth;
   a decay-time sensor adapted to respond to biological activity by generating a selective emission, said decay-time sensor spread along an interior surface of each said container;
   a single light source including a laser and an intensity modulator for generating a modulated output beam and a modulated reference beam;
   a light beam deflector for selectively directing said modulated output beam to a preselected one of said decay-time sensors to excite said decay-time sensors which generate said selective emission; and
   a detector for receiving said selective emission and said modulated reference beam and for monitoring a phase shift between said selective emission and said modulated reference beam said phase shift being correlated to said biological activity and being used to determine whether microorganism growth is present in each said container.

2. An apparatus as recited 1, wherein said light source is a green helium neon laser emitting in a wavelength range between 400 and 600 nm.

3. An apparatus as recited in claim 2, wherein said deflector is a two-dimensional galvanometric laser deflector.

4. An apparatus as recited in claim 3, wherein said sensor is adapted to react with a specimen sample.

5. An apparatus as recited in claim 4, wherein said sensor is a fluorescence sensor.

6. An apparatus as recited in claim 1, wherein said sensor is adapted to react with a specimen sample.

7. An apparatus as recited in claim 1, wherein said detector includes a collection lens and a photodetector.

8. An apparatus as recited claim 7, wherein said collection lens is a Fresnel lens.

9. An apparatus as recited in claim 7, wherein said photodetector is a photomultiplier.

10. An apparatus as recited in claim 7, wherein said detector includes a spectral filter to prevent laser light from reaching said photodetector.

11. An apparatus as recited in claim 1, further comprising a mirror for reflecting said output beam from said deflector to said preselected sensor.

12. An apparatus for detecting microorganisms in fluid specimen samples, said apparatus comprising:
    a plurality of sealable containers adapted to sustain microorganism growth;
    a fluorescence decay-time sensor adapted to respond to biological activity by generating a selective fluorescence emission, said fluorescence decay-time sensor spread along an interior surface of each said container to react with a specimen sample;
    a single high energy light source having an intensity modulator for generating a modulated output beam and a modulated reference beam;
    a light beam deflector for selectively directing said modulated output beam to a preselected one of said fluorescence decay-time sensors to excite said fluorescence decay-time sensors which generate said selective fluoresence emission; and
    a detector for receiving said selective fluoresence emission and said modulated reference beam for monitoring a phase shift between said selective fluorescence emission and said modulated reference beam said phase shift being correlated to said biological activity and being used to determine whether microorganism growth is present in each said container.

13. An apparatus as recited in claim 12, wherein said light source includes a laser.

* * * * *